(12) United States Patent
Han

(10) Patent No.: US 9,192,465 B2
(45) Date of Patent: Nov. 24, 2015

(54) INTRAOCULAR LENS INJECTOR

(75) Inventor: Myoung Soo Han, Cheongju-si (KR)

(73) Assignee: RET CO., LTD., Cheongwon-Gun, Chungcheongbuk-Do (KR)

( * ) Notice: Subject to any disclaimer, the term of this patent is extended or adjusted under 35 U.S.C. 154(b) by 930 days.

(21) Appl. No.: 12/856,816

(22) Filed: Aug. 16, 2010

(65) Prior Publication Data

US 2011/0313425 A1     Dec. 22, 2011

(30) Foreign Application Priority Data

Jun. 16, 2010   (KR) .................... 10-2010-0057056

(51) Int. Cl.
*A61F 2/16* (2006.01)

(52) U.S. Cl.
CPC ................................ *A61F 2/1678* (2013.01)

(58) Field of Classification Search
CPC .............................. A61F 2/1662; A61F 2/1678
USPC ........................................ 623/6.12; 606/107
See application file for complete search history.

(56) References Cited

U.S. PATENT DOCUMENTS

| | | | |
|---|---|---|---|
| 6,387,101 B1* | 5/2002 | Butts et al. | 606/107 |
| 2004/0238392 A1* | 12/2004 | Peterson et al. | 606/107 |
| 2006/0167466 A1* | 7/2006 | Dusek | 606/107 |
| 2008/0269770 A1* | 10/2008 | Pynson et al. | 606/107 |

* cited by examiner

*Primary Examiner* — Sarah W Aleman
(74) *Attorney, Agent, or Firm* — Kile Park Reed & Houtteman PLLC

(57) ABSTRACT

Disclosed herein is an intraocular lens injector for inserting an intraocular lens into an eye, the intraocular lens injector including: a cylindrical cylinder, into which a plunger for passing the intraocular lens to be guided into the eye is inserted; a connection block having a C-shaped longitudinal cross-section and integrally formed at the front end of the cylinder; a cartridge, which is connected to the connection block and includes first and second wing portions, which are folded with respect to each other, first and second receiving grooves formed at the connection portion of the first and second wing portions and having a semicircular longitudinal cross-section, and a truncated conical guide portion, which extends from the second receiving groove in the lateral direction and includes a guide passage having a circular cross-section corresponding to the shape of the assembled first and second receiving grooves; and a cover member inserted into the connection block together with the second wing portion of the cartridge and detachably connected to the connection block.

4 Claims, 4 Drawing Sheets

INTRAOCULAR LENS INJECTOR

CROSS-REFERENCE TO RELATED APPLICATION

This application claims priority to and the benefit of Korean Patent Application No. 10-2010-0057056, filed on Jun. 16, 2010, the disclosure of which is incorporated herein by reference in its entirety.

BACKGROUND

1. Field of the Invention

The present invention relates to an intraocular lens injector for inserting an intraocular lens into an eye in replacement of a crystalline lens extracted during cataract surgery, and more particularly, to an intraocular lens injector, in which a cartridge, in which an intraocular lens is placed, is integrally formed with a cylinder, in which a plunger slides, and the cartridge is slidably covered such that the intraocular lens can be kept or carried while being placed in the cartridge, thereby eliminating the inconvenience of connecting the cartridge including the intraocular lens to the cylinder during cataract surgery and facilitating the cataract surgery.

2. Discussion of Related Art

Cataract is a disease caused by opacity of the crystalline lens of the eye and may lead to blindness in severe cases. The cataract is classified into a congenital cataract present in utero or at birth, a senile cataract occurring in the aged, a generalized cataract caused by various diseases, and the like. Among them, the senile cataract is most frequently observed in the aged.

Methods for treatment of cataract include pharmacotherapy and surgery. Since there is no guarantee that the pharmacotherapy can completely cure the cataract, the cataract surgery is mainly used.

Cataract surgery methods include intracapsular extraction, in which the entire crystalline lens and its enclosing capsule are removed, and extracapsular extraction, in which the posterior capsule of the crystalline lens having a thickness of about 0.01 mm, which is located adjacent to the hyaloid, is left in place and the remaining crystalline lens is removed.

The intraocular lens is an artificial lens used to replace the natural crystalline lens of the eye when the natural lens has cataracts or is otherwise diseased. The intraocular lens is also sometimes implanted into an eye to correct refractive errors of the eye. The intraocular lens may be made of a variety of materials or combinations of materials such as poly(methyl methacrylate) (PMMA), silicone, hydrogel, silicone hydrogel, etc.

In order to implant the intraocular lens into the eye, the sclera of the eye is incised, and a viscoelastic material is injected into the sclera to protect the anterior tissues. Then, the upper part of the lens capsule is incised to remove the clouded lens. Subsequently, the clouded lens nucleus is completely removed from the lens capsule, and the intraocular lens is injected into the lens capsule while injecting the viscoelastic material into the lens capsule to facilitate the insertion of the intraocular lens. The intraocular lens is injected into the lens capsule in a folded or rolled state and then restored to its original state, during which an intraocular lens injector is used.

The above-described intraocular lens injector has a structure in which a cartridge in which an intraocular lens in a folded or rolled state is placed and a cylinder for pushing the intraocular placed in the cartridge to the eye are separated from each other, and thus it is inconvenient to connect the cartridge and the cylinder for the use of the intraocular lens injector. Moreover, the intraocular lens preloaded into the cartridge is inserted into the eye by pushing the cylinder during cataract surgery on the eye from which the crystalline eye is extracted, which increases the difficulty of the surgery.

Various studies have been carried out to solve the above problems, various studies have been conducted to in progress in recently years, but there is no clear solution yet.

SUMMARY OF THE INVENTION

The prevent invention has been made in an effort to solve the above-described problems associated with the prior art, and an object of the present invention is to provide an intraocular lens injector, in which an intraocular lens is placed on first and the second receiving grooves of a cartridge and enclosed within the first and second receiving grooves by a cover member which is inserted into a connection block together with a second wing portion of the cartridge and detachably connected to the connection block, thus enabling effective handling during surgery or distribution.

To accomplish the above objects of the present invention, there is provided an intraocular lens injector for inserting an intraocular lens into an eye, the intraocular lens injector including: a cylindrical cylinder, into which a plunger for passing the intraocular lens to be guided into the eye is inserted; a connection block having a C-shaped longitudinal cross-section and integrally formed at the front end of the cylinder; a cartridge, which is connected to the connection block and includes first and second wing portions, which are folded with respect to each other, first and second receiving grooves formed at the connection portion of the first and second wing portions and having a semicircular longitudinal cross-section, and a truncated conical guide portion, which extends from the second receiving groove in the lateral direction and includes a guide passage having a circular cross-section corresponding to the shape of the assembled first and second receiving grooves; and a cover member inserted into the connection block together with the second wing portion 43 of the cartridge 40 and detachably connected to the connection block.

The cover member may include a handle portion, first and second locking flanges formed at both sides of the handle portion, and a slide portion extending from the first and second locking flanges.

The slide portion may include an inclined portion at the end thereof, which is inclined to one side, to simultaneously cover the first and second receiving grooves even when the first and second receiving grooves are partially open.

The inclined portion may have a width smaller than that of the slide portion to be easily detachable.

The inclined portion may include an upwardly bent portion at the end thereof and is connected to a base end of the first receiving groove in a reclining manner so as to facilitate the removal of the cover member having the inclined portion when the first wing portion having the first receiving groove is inwardly folded.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
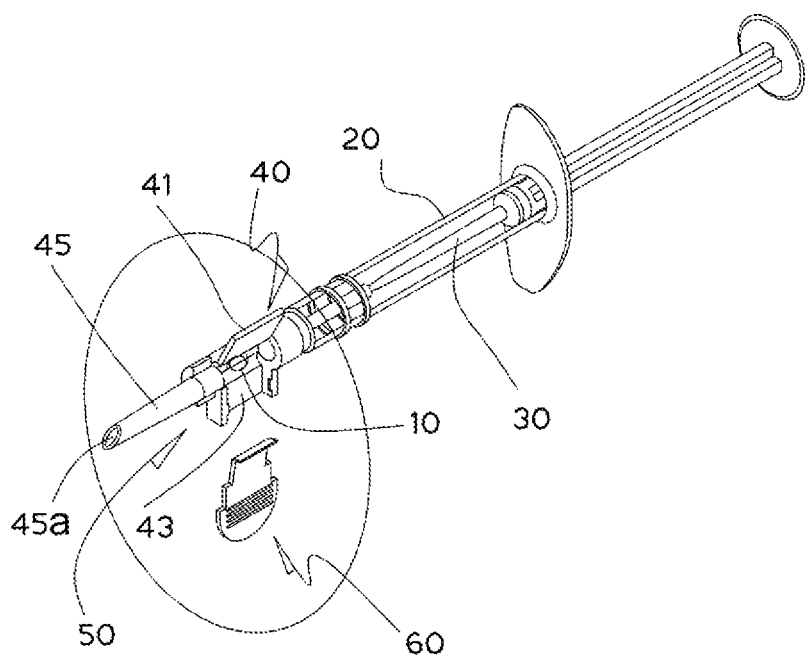
FIG. 1 is a perspective view showing an intraocular lens injector in accordance with the present invention in which a cartridge and a cover member are connected to each other.

Hereinafter, exemplary embodiments of the present invention will be described in detail below with reference to the accompanying drawings such that those skilled in the art to which the present invention pertains can easily practice the present invention.

The configuration of an intraocular lens injector of the present invention will be described below.

The intraocular lens injector for inserting an intraocular lens 10 into an eye of the present invention includes: a cylindrical cylinder 20, into which a plunger 30 for passing the intraocular lens 10 to be guided into the eye is inserted; a connection block 50 having a C-shaped longitudinal cross-section and integrally formed at the front end of the cylinder 20; a cartridge 40, which is connected to the connection block 50 and includes first and second wing portions 41 and 43, which are folded with respect to each other, first and second receiving grooves 41a and 43a formed at the connection portion of the first and second wing portions 41 and 43 and having a semicircular longitudinal cross-section, and a truncated conical guide portion 45, which extends from the second receiving groove 43a in the lateral direction and includes a guide passage 45a having a circular cross-section corresponding to the shape of the assembled first and second receiving grooves 41a and 43a; and a cover member 60 inserted into the connection block 50 together with the second wing portion 43 of the cartridge 40 and detachably connected to the connection block 50.

The cover member 60 includes a handle portion 61, first and second locking flanges 61a and 61b formed at both sides of the handle portion 61, and a slide portion 63 extending from the first and second locking flanges 61a and 61b.

The slide portion 63 includes an inclined portion 65 at the end thereof to simultaneously cover the first and second receiving grooves 41a and 43a even when the first and second receiving grooves 41a and 43a are partially open.

The inclined portion 65 has a width smaller than that of the slide portion 63 to be easily detachable.

Moreover, the inclined portion 65 has an upwardly bent portion 67 at the end thereof and is connected to a base end of the first receiving groove 41 a in a reclining manner so as to facilitate the removal of the cover member 60 having the inclined portion 65 when the first wing portion 41 having the first receiving groove 41 a is inwardly folded.

Here, the first and second receiving grooves 41a and 43a may have a different configuration depending on the use of the intraocular lens 10 and the specifications such as the shape and size.

An example of the intraocular lens injector having the above-described configuration will be described as follow.

Figure 2:
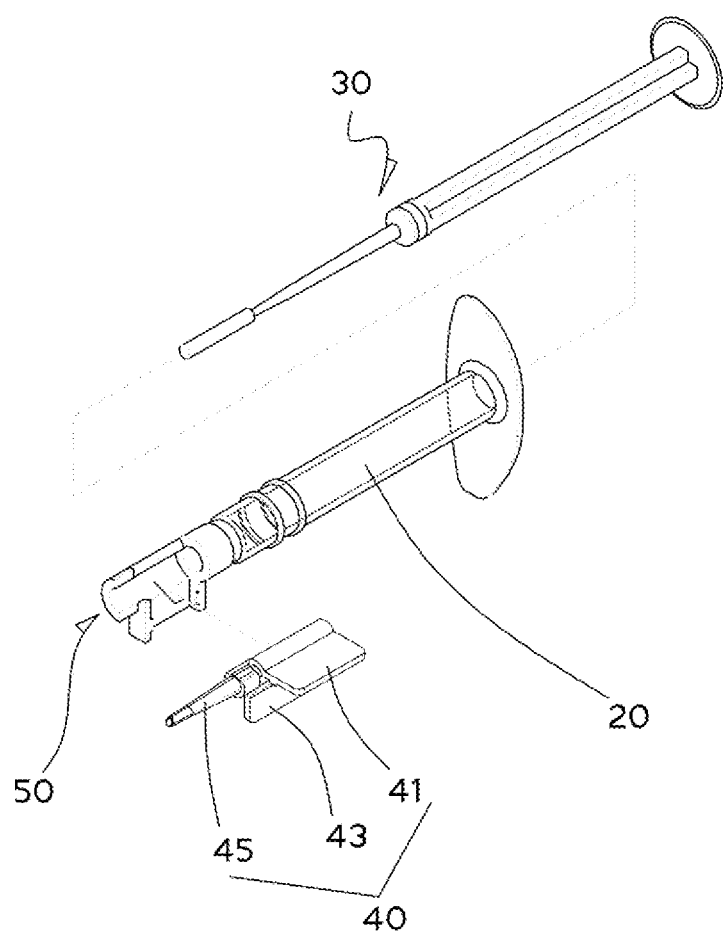
FIG. 2 is an exploded perspective view showing the intraocular lens injector in accordance with the present invention of FIG. 1.
Figure 3:
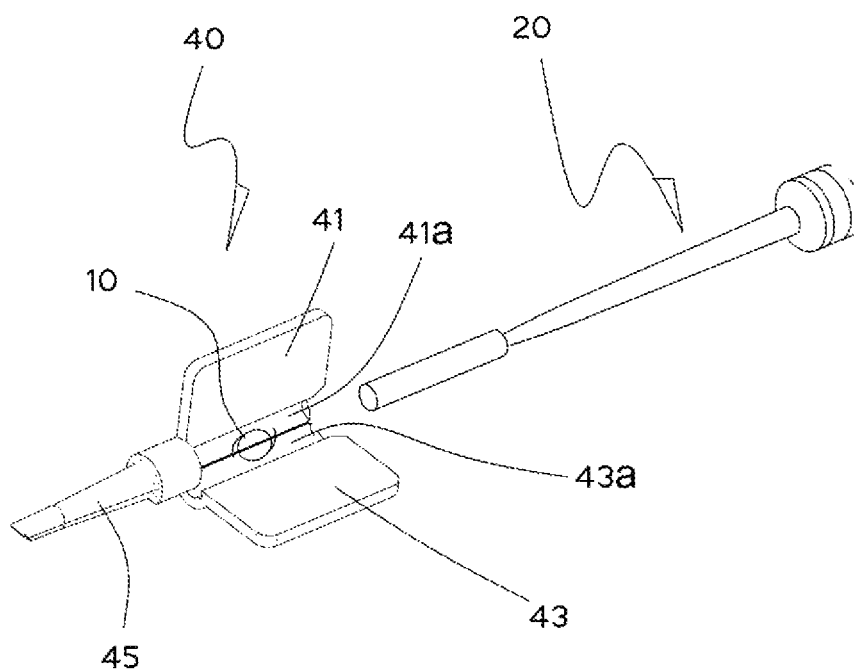
FIG. 3 is an exploded perspective view showing that an intraocular lens is guided by a cartridge and a plunger in accordance with the present invention.
Figure 4:
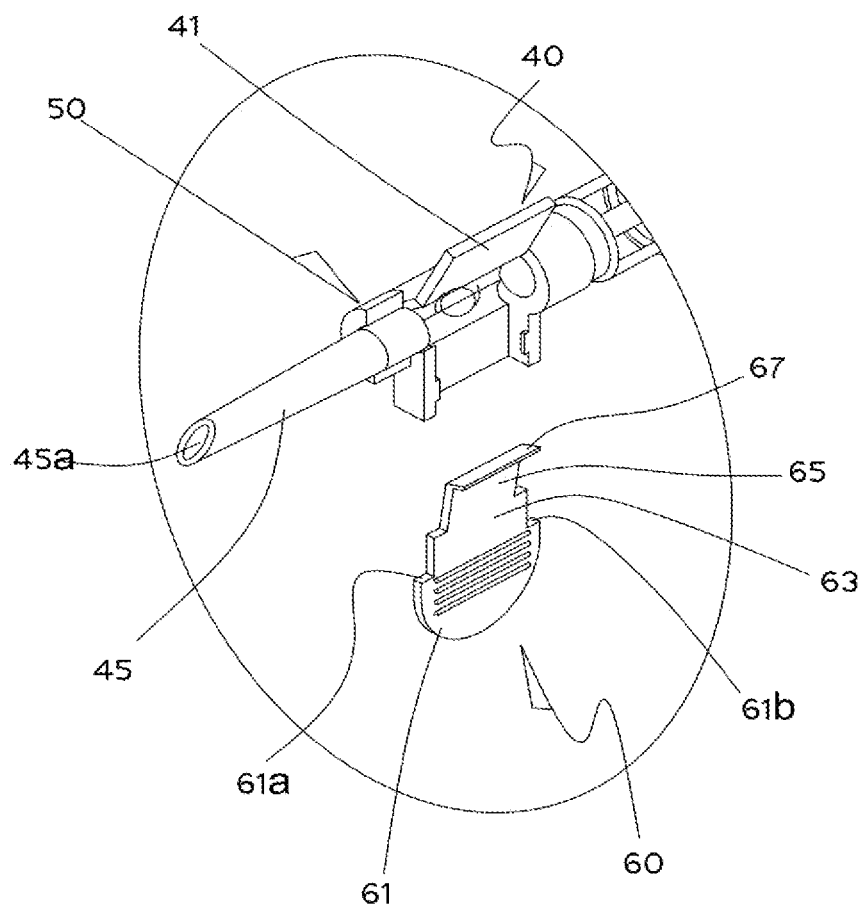
FIG. 4 is an enlarged perspective view of the main portions of FIG. 1.

FIGS. 1 and 2 are perspective views showing the intraocular lens injector in accordance with the present invention in which the cartridge 40 and the cover member 60 are connected to each other.

First, in order to insert the intraocular lens 10 into the eye of a cataract patient, the intraocular lens 10 placed on the first and the second receiving grooves 41a and 43a of the cartridge 40 is moved into the guide passage 45a of the truncated conical guide portion 45 by pushing the plunger 30.

Subsequently, the intraocular lens 10 moved into the guide passage 45a is pressed close to the eye of the cataract patient using the plunger 30 and an elastic bush connected to the front end of the plunger 30 and then inserted into the eye of the cataract patient After the intraocular lens 10 is inserted into the eye, the intraocular lens injector is discarded.

As such, the present invention provides a preset type intraocular lens injector, in which the intraocular lens 10 is placed on the first and the second receiving grooves 41 a and 43a of the cartridge 40 and enclosed within the first and second receiving grooves 41a and 43a by the cover member 60.

As described above, according to the present invention, with the use of an intraocular lens injector, it is possible to perform emergency surgery and, at the same time, the intraocular lens injector can be distributed in a state where the cartridge and the cover member are sterilized and vacuum packed with foil.

Accordingly, the intraocular lens injector can be mass-produced and commercialized.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An intraocular lens injector for inserting an intraocular lens into an eye, the intraocular lens injector comprising:
    a cylindrical cylinder, into which a plunger for passing the intraocular lens to be guided into the eye is inserted;
    a cartridge, which includes first and second wing portions, which are able to move between open and closed positions, first and second receiving grooves formed at a connection portion of the first and second wing portions and having a semicircular longitudinal cross-section, and a truncated conical guide portion, which extends from the second receiving groove and includes a guide passage having a circular cross-section corresponding to the shape of the assembled first and second receiving grooves;
    a connection block having a C-shaped longitudinal cross-section and integrally formed at the front end of the cylinder and shaped to receive the cartridge in the open position; and
    a cover member inserted into the connection block to cover the second wing portion of the cartridge while the first and second wing portions are in the open position, and detachably connected to the connection block by sliding locking flanges into receiving means of the connection block,
    wherein the cover member comprises a handle portion disposed in a planar space, first and second locking flanges formed in the planar space at both sides of the handle portion, and a slide portion extending from the planar space of the first and second locking flanges.

2. The intraocular lens injector of claim 1, wherein the slide portion comprises an inclined portion at an end of the slide portion, which is inclined to one side, to simultaneously cover the first and second receiving grooves even when the first and second receiving grooves are partially open.

3. The intraocular lens injector of claim 2, wherein the inclined portion has a width in a direction same as a longitudinal direction of the intraocular lens injector, and the width of the inclined portion is smaller than that of the slide portion to be easily detachable.

4. The intraocular lens injector of claim 2, wherein the inclined portion comprises an upwardly bent portion which is disposed to be in contact with the first wing portion in a reclining manner so as to facilitate the removal of the cover member having the inclined portion when the first wing portion is inwardly folded toward the second wing portion.

* * * * *